(12) United States Patent
Ou et al.

(10) Patent No.: US 6,489,527 B1
(45) Date of Patent: Dec. 3, 2002

(54) PROCESS FOR IMPROVING PURITY OF PARA-XYLENE PRODUCT

(76) Inventors: John Di-Yi Ou, 14643 Redwood Bend Trail, Houston, TX (US) 77062; Harold William Helmke, 3807 Fawn Creek, Kingwood, TX (US) 77339; Dana Lynn Pilliod, 2104 Brook Haven Dr., League City, TX (US) 77573

(*) Notice: Subject to any disclaimer, the term of this patent is extended or adjusted under 35 U.S.C. 154(b) by 1314 days.

(21) Appl. No.: 08/575,443

(22) Filed: Dec. 20, 1995

Related U.S. Application Data

(63) Continuation of application No. 08/106,326, filed on Aug. 13, 1993, now abandoned, which is a continuation-in-part of application No. 07/888,577, filed on May 26, 1992, now abandoned.

(51) Int. Cl.[7] .............................. C07C 2/66; C07C 7/00
(52) U.S. Cl. ...................................... 585/467; 585/805
(58) Field of Search ................................ 585/467, 805

(56) References Cited

U.S. PATENT DOCUMENTS

| | | | | |
|---|---|---|---|---|
| 2,585,525 A | * | 2/1952 | Yates | 585/805 |
| 2,648,713 A | | 8/1953 | Schneider | 260/674 |
| 2,801,271 A | | 7/1957 | Schlatter | 260/674 |
| 2,816,940 A | * | 12/1957 | Schlatter | 585/805 |
| 2,840,621 A | | 6/1958 | Corson et al. | 260/674 |
| 3,539,650 A | | 11/1970 | Amir | 260/674 |
| 3,770,841 A | * | 11/1973 | Meyers, Jr. | 585/805 |
| 3,793,385 A | * | 2/1974 | Bond et al. | 585/805 |
| 3,813,452 A | * | 5/1974 | Bieser | 585/805 |
| 4,002,697 A | * | 1/1977 | Chen | 585/454 |
| 4,021,499 A | * | 5/1977 | Bieser | 585/805 |
| 4,100,215 A | * | 7/1978 | Chen | 585/467 |
| 4,584,422 A | * | 4/1986 | Barile et al. | 585/481 |
| 5,055,630 A | | 10/1991 | Puppel | 585/814 |
| 5,177,295 A | * | 1/1993 | Oroskar et al. | 585/805 |

FOREIGN PATENT DOCUMENTS

| GB | 1108178 | * | 4/1968 |
|---|---|---|---|

OTHER PUBLICATIONS

D. Nightingale, et al., "Orientation Effects in the Alkylation of m–Xylene by Various Procedures and Reagents," *Journal of the American Chemical Society*, vol. 64, pp. 1662–1665, Jul. 1942.

D. Nightingale, et al., "The Alkylation of o– and p–Xylene," *Journal of the American Chemical Society*, vol. 66, pp. 154–155, Jan., 1942

B. B. Corson, et al., "Separation of Positional Isomeric Dialkylbenzenes," *Industrial and Engineering Chemistry*, vol. 48, No. 7, pp. 1180–1182, Jul. 1956.

Chemical Abstract 116(6):43394n (1992).

* cited by examiner

*Primary Examiner*—Walter D. Griffin

(57) ABSTRACT

A process for producing 99.5+ wt. % para-xylene by selective alkylation has been discovered. A mixture of isomers of para-xylene having at least about 90.0 wt. % purity may be reacted with an alkylating agent having at least one tertiary butyl moiety in the presence of an acidic catalyst under conditions where the catalyst is in good molecular contact with the non-para-xylene isomers. The catalyst may be a high surface area acidic heterogeneous catalyst such as a proton-exchanged zeolite. Upon distillation, para-xylene is recovered in 99.5 wt. % purity or higher. The selective alkylation gives little or no alkylation of the para-xylene, the most predominant species, and very little or no isomerization to the other, non-desirable isomers.

35 Claims, No Drawings

PROCESS FOR IMPROVING PURITY OF PARA-XYLENE PRODUCT

This is a continuation, of application Ser. No. 08/106,326, filed Aug. 13, 1993, now abandoned, which is a continuation in part of application Ser. No. 07/888,577, filed May 26, 1992, now abandoned.

FIELD OF THE INVENTION

The invention relates to methods for producing para-xylene, and more particularly, the invention relates, in one aspect, to processes for purifying para-xylene in exceptionally high purity from its isomers.

BACKGROUND OF THE INVENTION

There exist several technologies for recovering para-xylene from its mixture with its isomers which are ortho-xylene, meta-xylene and ethylbenzene. Adsorption-based methods and crystallization-based processes are commonly used in industry. These two processes can produce 99.6 to 99.8 wt. % purity para-xylene very efficiently. Achieving purities on the order of 99.9+ wt. %, however, is very difficult and costly. Other techniques for xylene separation such as hydrogen-fluoride extraction, sulfonation and alkylation have not been able to demonstrate an efficiency comparable to that of the adsorption and crystallization processes.

The chemistry for xylenes alkylation has been studied for several decades. D. Nightingale, et al. in "Orientation Effects in the Alkylation of m-Xylene by Various Procedures and Reagents," *Journal of the American Chemical Society*, Vol. 64, pp. 1662–1665, 1942; and D. Nightingale, et al. in "The Alkylation of o- and p-Xylene," *Journal of the American Chemical Society*, Vol. 66, pp. 154–155, 1944, indicate that ortho-xylene, meta-xylene and ethylbenzene can be alkylated with molecules containing tertiary butyl moiety (e.g. isobutylene, tertiary butyl chloride, tertiary butyl benzene, di-tertiary butyl hydroxyl toluene, etc.). para-Xylene, however, was found to be quite difficult for tertiary butylation. It is theorized that a steric effect has hindered the insertion of the bulky tertiary butyl group to the more restricted aromatic ring of the para-xylene molecule. Partial separation of para-xylene from meta-xylene and ortho-xylene based on the selective alkylation concept has been demonstrated; see, e.g., U.S. Pat. Nos. 2,648,713, 2,801,271 and B. B. Corson, et al., *Industrial and Engineering Chemistry*, Vol. 48, No. 7, pp. 1180, 1956.

U.S. Pat. No. 2,648,713 provides a process for the separation of ortho-xylene from an admixture thereof with meta-xylenes by the successive steps of alkylation, distillation and dealkylation. para-Xylene may also be present in the xylene mixture and remains unalkylated with the meta-xylene. The alkylating agent is preferably an olefin or cycloolefin having a tertiary carbon atom, such as isobutylene; diisobutylene; trimethylethylene 2,4-methylpentene-2; 3-methylbutene-2; 4-methylcyclohexene-1 and 1-methylcyclohexene-1. This process, as the ones previously discussed, is limited to bulk separation; in the best Example recorded therein (Example 2) the percent conversion of ethyl benzene and ortho-xylene was 89 and 54, respectively.

U.S. Pat. No. 2,801,271 describes an integrated process for separating xylene isomers and producing high octane gasoline which involves contacting isobutylene with a xylene fraction having substantial quantities of para-xylene and meta-xylene. The contact is done in the presence of liquid hydrogen fluoride at a temperature in the range x10 to 100° C. The quantity of isobutylene employed is sufficient to alkylate a substantial proportion of the meta-xylene contained in the xylene fraction. The alkylation reaction product is fractionally distilled to separate a para-xylene rich fraction and a fraction comprising tertiary-butyl-meta-xylene. The latter fraction and a straight run petroleum distillate are contacted with a silica-alumina catalyst in a catalytic cracking zone at a temperature in the range 800 to 1000° F. The latter fraction is cracked forming predominantly meta-xylene and isobutylene. The effluent from the cracking zone is fractionally distilled to separate a fraction rich in isobutylene, and the isobutylene rich fraction is then returned together with additional xylenes to the alkylation step. Again, this process is a bulk separation process; the only example (Example 1) to the alkylation separation step yielded a para-xylene purity of 48%.

Purified meta-xylene is obtained by alkylating a mixture containing m- and p-xylene with a small but effective amount of isopropylating agent in the presence of a small but sufficient amount of aluminum chloride catalyst, according to U.S. Pat. No. 3,539,650. The alkylation mixture is maintained at a temperature within the range of about 70° C. to about 100° C. for about thirty minutes to one hour after which the catalyst is destroyed, an isopropyl meta-xylene fraction recovered, and the recovered fraction deisopropylated to produce meta-xylene above 95% purity. It is apparent that meta-xylene concentrations much above 98% may not be readily attainable, however, given the best Examples in Table IV of this patent, which focuses only on the meta-xylene product, rather than the para-xylene material.

U.S. Pat. No. 5,055,630 describes a process for obtaining a para-xylene final product more than 98% pure from a crystalline starting material with a purity of about 98%, which includes the steps of intermixing the starting material with precooled water and feeding back the recovered para-xylene in a mixer at a temperature of 0 to 13° C. to form a para-xylene-crystal-water mixture containing para-xylene crystals and water. The mixture is continuously transferred as soon as it contains 30% by weight para-xylene crystals into a purifying centrifuge via a dewatering filter to form a fluid phase and a para-xylene crystal slurry. The fluid phase is separated further from the para-xylene crystals in a first stage of a purifying centrifuge, mixing the para-xylene crystal slurry in a second stage with a partial flow of final product, heating at about 13° C. and subsequently liberating from the fluid phase still adhering, whereby the para-xylene crystals are drawn off into the heated vessel. Next, the para-xylene crystals melted in the heated vessel are drawn off as the final product with the desired purity. A partial flow of final product is also drawn off which is fed back to the second stage of the purifying centrifuge, being heated previously to a temperature from 60 to 80° C. and feeding the fluid phase separated from the para-xylene crystals to the second stage of the centrifuge for recovery of additional para-xylene which becomes part of the final product stream. It would be advantageous if a method could be devised for obtaining high purity para-xylene which was less complex and costly than that described in U.S. Pat. No. 5,055,630.

The separation of close-boiling meta-xylene and para-xylene via selective alkylation and subsequent dealkylation or transalkylation was recently studied according to *Chemical Abstract* 116(6):43394n (1992). The alkylation was carried out with isobutylene or diisobutylene with concentrated $H_2SO_4$ catalyst at −10 to +20° and Filtrol-24 acid clay at 80–130°, respectively. meta-Xylene reacted very selectively (Filtrol-24 gave selectively 5-tert-butyl-meta-xylene), and the alkylated products could be dealkylated at higher temperatures in the presence of Filtrol-24 catalyst, to give relatively pure meta-xylene and isobutylene which could be recycled. para-Xylene purity is not mentioned in the Abstract.

There remains a need for a process which provides a high yield to para-xylene in very high purity which is relatively simple and cost-effective. The linking of two conventional para-xylene purification processes together is generally less efficient. Additionally, the reaction to make para-xylene is reversible under many of the conditions to selectively alkylate the xylene mixture; often in the attempt to make very high purity para-xylene, an isomerization side reaction occurs to make more of the less desirable meta-xylene and/or ortho-xylene. At relatively high purities, e.g. 98 wt. %, attempts to increase purity of the already pure product result in degradation of the product rather than improvement through these side reactions. Also, para-xylene does alkylate to some extent and there is a great tendency when 98 wt. % of the product is para-xylene that the alkylation will more readily occur with the para-xylene, rather than with the small proportion of impurities which are more difficult for the catalyst to come into contact with. Attempts often result in removing alkylated para-xylene and/or isomerizing para-xylene with the overall result of a relatively increased proportions of impurity and a product with a lowered purity to para-xylene.

Many of the prior processes do not discuss the problems of side reactions and reversible reactions. Most of them only are concerned only with bulk separations and are satisfied with conversions of about 50%. As discussed, only U.S. Pat. No. 5,055,630 attempts to achieve high purity para-xylene, and it is only accomplished via a complicated crystallization process involving a multi-stage centrifuge. It is anticipated that in the near future there will be a great need for ultra-pure para-xylene, on the order of 99.9+ wt. % purity.

SUMMARY OF THE INVENTION

Accordingly, it is an object of the present invention to provide a process for recovering para-xylene in at least 99.5 wt. % purity, and to 99.9+ wt. % purity, if desirable.

It is another object of the present invention to provide a process for giving para-xylene in very high purity by selective alkylation in a straight-forward, simple manner.

Another object of the present invention is to provide a process for yielding para-xylene in very high purity by selective alkylation with extremely high selectivity and little or no reverse reactions and side reactions.

In carrying out these and other objects of the invention, there is provided, in one form, a reactive purification employing selective alkylation for producing at least 99.5 wt. % para-xylene from a mixture of isomers of para-xylene having more than about 90 wt. % para-xylene and the mixture being produced by a process exclusive of a selective alkylation process. The purification process involves (a) alkylating substantially all of the isomers of para-xylene in the mixture of xylene isomers with an alkylating agent, while alkylating substantially none of the para-xylene; and (b) separating the para-xylene in at least 99.5 wt. % purity and at least greater than the concentration of para-xylene in the mixture of xylene isomers, from the alkylated xylene isomers to give the final product stream.

The present invention is distinct from U.S. Pat. No. 5,055,630, described earlier, in that the former purifies via alkylation whereas the latter uses crystallization. Although it is possible in some prior processes to achieve 99.9 wt. % purity, it is accomplished only with a significant capacity debit. For example, in one conventional process, the increase from producing 99.8 to 99.9 wt. % para-xylene results in a 15% reduction in capacity. That is, there is a production capacity/purity trade off which cannot be overcome. Prior commercial processes are separation processes only, whereas the subject process uses reactive purification and reaction processes. In the present invention, one does not have to sacrifice capacity to increase purity.

DETAILED DESCRIPTION OF THE INVENTION

It has been discovered that it is not economical nor efficient to produce 99.9+ wt. % para-xylene via any single separation process, whether adsorption, crystallization, hydrogen-fluoride extraction, sulfonation or other processes. It has been surprisingly found that the best process arrangement to maximize purity and productivity appears to be attaching an alkylation process at the back end of an adsorption or crystallization process. Such a hybrid system can easily achieve the desired 99.5+ wt. % purity without any significant productivity loss. Of course, the final para-xylene purity must be greater than that of the mixture of xylene isomers before purification.

In the first treatment of the hybrid system, a conventional para-xylene recovery technology such as the PAREX® adsorption process or a crystallization process will be used to produce a product stream with 99.0 to 99.8 wt. % para-xylene. PAREX is a registered trademark of UOP Inc. Other processes that produce a mixture of isomers of para-xylene include, but are not necessarily limited to, hydrogen fluoride extraction, sulfonation, fractionation, membrane separation and selective toluene disproportionation (STDP). Essentially, the method of this invention can be used to purify a mixture of isomers of para-xylene produced by any process known in the art except or exclusive, of a selective alkylation process. Such mixtures of isomers para-xylene may contain more than about 90 wt. % para-xylene, alternatively from 90 to 99.9 wt. % para-xylene, in one embodiment from 95 to 99.9 wt. % para-xylene and in a narrower range from 98 to 99.9 wt. % para-xylene. These commercial processes are very efficient in such purity ranges. As explained, what is more difficult is how to upgrade the product purity to 99.5+ wt. % efficiently. Unexpectedly, it was discovered that further para-xylene purification is better done via xylene-selective alkylation; the second treatment of the hybrid system of this invention. An acidic catalyst is used to selectively alkylate just the ethylbenzene, meta-xylene and ortho-xylene while leaving para-xylene alone unalkylated. Since the alkylated para-xylene isomers boil at substantially higher temperatures compared to unalkylated para-xylene, a simple post-alkylation fractionation or a post alkylation carbon adsorption provides efficient removal of the heavies and produce 99.5+ wt. % para-xylene. Moreover, the inventive process does not have appreciable side reactions, reverse reactions, or alkylation of para-xylene which decreases yield or conversion to high purity para-xylene.

The purification via alkylation process of this invention can be accomplished with either an acidic heterogeneous catalyst, such as proton-exchanged zeolites or an acidic homogeneous catalyst such as aluminum chloride at a temperature ranging from about 1 to 300° C. preferably between about 1 to about 100° C., most preferably between about 10 to about 50° C. and a pressure from sub-atmospheric to 1000 psig, in one embodiment. In one embodiment, the LHSV ranges from about 0.1 to about 100, and preferably ranges from about 0.1 to about 10.

The selective alkylation may, in one embodiment, be done in the presence of an acidic catalyst. Preferably, steps are taken so that there is good molecular contact between the catalyst and the xylene isomers which are not para-xylene. Without being bound by any one theory, it is hypothesized that the success of the present invention is due at least in part to excellent molecular contact between the catalyst and the non-para-xylene isomers. This contact may involve a particular high surface area catalyst, extensive mixing or both. Extensive mixing includes, but is not limited to mixing by pressure drop, mixing orifices, static mixers, distribution heads and high speed mixing mechanisms. By "high surface area" is meant a catalyst having a surface area in excess of about 100 $m^2/g$ and in one embodiment in excess of about 200 $m^2/g$, and preferably one with a surface area in excess of about 300 $m^2/g$. A most preferred high surface area catalyst has a surface area in excess of about 450 $m^2/g$. Additionally, the catalyst should be one which does not polymerize the alkylating agent. For example, the catalysts should not be one which substantially dimerizes isobutylene, if this is the alkylation agent.

In one embodiment, the catalyst is a high surface area heterogeneous catalyst, and more preferably may be a high surface area catalyst including, but not necessarily limited to, proton-exchanged zeolites, bentonite clay, acid-treated clay, acidic alumina, solid acids, proton-exchanged resins, and the like. The most preferable catalysts are proton-exchanged zeolites. In another embodiment of the invention, homogeneous acidic catalysts suitable for this invention include, but are not limited to, aluminum chloride, alkyl aluminum chlorides, hydrofluoric acid, sulfuric acid and the like.

The selective alkylation step of the present invention may be conducted at a temperature in the range of from about 10 to about 300° C., preferably from about 10 to about 150° C. and most preferably from about 10 to 50° C. Reaction temperatures greater than about 300° C. are not desired as the tendency for isomerization increases with increasing temperature (the para-xylene isomerizes to ortho-xylene, meta-xylene and/or ethylbenzene), as does the undesired alkylation of para-xylene. The alkylation reaction may be conducted in the liquid phase or the vapor phase and thus may be conducted from sub-atmospheric to about 1000 psig, preferably from sub-atmospheric to about 500 psig, and most preferably from subatmospheric to about 300 psig. Further, the best alkylating agents were found to contain at least one tertiary butyl moiety. In one embodiment, the alkylating agent is selected from the group consisting of isobutylene, tertiary butyl chloride, tertiary butyl benzene, di-tertiary butyl hydroxyl toluene, isobutylene oligomers and the like. The amount of alkylating agent is dependent on other parameters; for example, it is necessary to have enough alkylating agent to react with all of the impurities. Thus, the amount of alkylating agent should be an effective amount to so alkylate the impurities desired to be removed. A large excess of alkylating agent should be avoided.

Under the conditions of this invention, the loss of para-xylene to alkylation is only in the range of several tenths of one percent. That is, the selectivity of alkylation of non-para-xylene isomers to para-xylene is a surprising 300:1 to 3000:1 ratio. Even a relatively high ratio of 30:1 would be unacceptable inasmuch as too much of the para-xylene would be lost, as has been established in the prior art. In prior processes, the selectivity was always less than 100:1; the selectivities achievable with this process are surprisingly higher. The selectivity achieved with this invention is unexpected and extraordinary. The process of this invention prevents destruction of the major product while selectively removing only the contaminants. This is unusual as all previous selective alkylation processes are not this selective, but rather only selectively alkylates the non-para-xylene isomers to a much lower extent than in this process. The system of this invention avoids (1) isomerization of the desired para-xylene and (2) alkylation of the para-xylene (even in the presence of high concentrations thereof), and (3) polymerization of the alkylating agent, e.g. dimerization of the isobutylene. Only by avoiding these other reactions are the extraordinarily high selectivities achieved using the inventive process which sets it apart from conventional processes which can only achieve a lower selectivity ratio.

Another advantage of the present invention is that the t-butyl-meta-xylene and -ortho-xylene adducts which may have a lower value will not have a significant effect on the process economics due to the low levels produced. Thus, although some small amount of lower value byproducts are produced, the process remains economically attractive. The purification method of this invention may be expanded so that the purified para-xylene may be further purified using an additional selective alkylation step to achieve ultrapure para-xylene.

That is, after the production of para-xylene by more than of 90 wt. % purity by any of the conventional methods, the purification process of this invention could be applied to the mixture of xylene isomers two or more times in series to achieve small increments of yet higher purity.

The invention will be illustrated more completely by the following Examples, which are not intended to limit the invention, but are simply instructive thereto.

EXAMPLE 1

The para-xylene product from Exxon Chemical PAREX® Adsorption Units (PAU) was used to evaluate the invention. The PAU para-xylene contained 99.70 wt. % para-xylene, 0.15 wt. % meta-xylene, 0.10 wt. % ethylbenzene and 0.05 wt. % ortho-xylene. The alkylation catalyst in this test was a proton-exchanged Y zeolite in the form of extrudate (LZY-82, obtained from UOP Inc.). The catalyst was calcined at 300° C. under nitrogen prior to testing. The alkylation reactor was a 0.5" I.D. and 3.0" long stainless steel tubing packed with 2.91 g calcined catalyst. A feed solution containing 99.70 wt. % PAU-para-xylene and 0.30 wt. % isobutylene was pumped through the reactor at 1 liquid hourly space velocity (LHSV), ambient temperature and 200 psig. Gas chromatograph analysis revealed that the alkylation product contained 0.08 wt. % $C_4$ compounds, 0.01 wt. % ethylbenzene, 0.05 wt. % meta-xylene, 99.36 wt. % para-xylene and 0.50 wt. % butylated xylenes and other heavy compounds. ortho-Xylene was completely butylated. After distillation to remove the $C_4$-materials and the heavies, a para-xylene product containing 0.01 wt. % ethylbenzene, 0.05 wt. % meta-xylene and 99.94 wt. % para-xylene can be obtained.

EXAMPLE 2

This Example was conducted similarly to Example 1. The catalyst was an extrudate of 80 wt. % proton-exchanged ultra stable Y zeolite (VALFOR CP304-37, obtained from The PQ Corp.) and 20 wt. % bentonite clay (obtained from Aldrich Co.). The catalyst was ground to 18/30 mesh and calcined at 300° C. prior to loading in the 0.5"×3.0" reactor. A feed solution composed of 99.50 wt. % PAU-para-xylene and 0.50 wt. % di-tertiary butyl hydroxyl toluene was pumped through the reactor at 0.5 LHSV, ambient temperature and 200 psig. The alkylation product contained 0.01 wt. % $C_4$ compounds, 0.01 wt. % ethylbenzene, 0.09 wt. % meta-xylene, 99.00 wt. % para-xylene, 0.89 wt. % alkylated xylenes and heavies. There was no ortho-xylene detected. After distillation, a para-xylene product containing 0.01 wt. % ethylbenzene, 0.09 wt. % meta-xylene and 99.90 wt. % para-xylene was obtained, as analyzed by gas chromatograph.

COMPARATIVE EXAMPLE 3

This Example demonstrates the fact that a simple extension of a previously known xylenes-alkylation technique is not suitable for the present purpose of producing 99.9+ wt. % purity para-xylene. The Example includes the following two experiments.

(A) Experiment A demonstrates the feasibility of using a conventional alkylation technique for the bulk separation of xylene mixtures. A mixture of 50.00% para-xylene and 50.00% ortho-xylene was prepared. 3.09 Grams of the mixture was then thoroughly mixed with 3.02 g. of tertiary-butyl chloride in a sealed vial. After the mixing, about 0.10 g. of aluminum chloride catalyst was added to the solution. The system was allowed to react at ambient conditions for 30 minutes. A sample of the hydrocarbon phase was taken and analyzed using gas chromatography. It was found that the xylenes fraction of the reaction product contained 97.50 wt. % para-xylene and 2.50 wt. % ortho-xylene indicating a good separation from the original 50.00% para-xylene and 50.00% ortho-xylene.

(B) Experiment B demonstrates the failure of using a conventional alkylation technique for producing para-xylene in very high purity. 39.91 Grams of a high purity para-xylene stream (99.70% para-xylene, 0.18% meta-xylene, 0.07% ethylbenzene and 0.05% ortho-xylene) was mixed with 0.11 g. tertiary butyl chloride. 5.00 Grams of the mixture was then brought into contact with 0.46 g. of aluminum chloride catalyst. The mixture was then allowed to react at ambient conditions for 30 minutes. A sample of hydrocarbon phase was analyzed using gas chromatography. The xylenes fraction of the reaction product contained 99.53% para-xylene, 0.32% meta-xylene, 0.09% ortho-xylene and 0.06% ethylbenzene. It is apparent that the alkylation was accompanied by a small amount of side reactions such as para-xylene isomerization; note the increase in meta-xylene and ortho-xylene fractions. As a result, the product had more isomers and para-xylene purity decreased. Such low levels of side reactions would not even be detected in bulk separations. But they would be detrimental for purifying high purity products and, as shown, overall para-xylene purity would decrease.

EXAMPLE 4

This Example illustrates the use of a homogeneous catalyst for purifying para-xylene. 20.00 Grams of a PAU para-xylene product (99.69% para-xylene, 0.18% meta-xylene, 0.07% ethylbenzene, 0.06% ortho-xylene) was thoroughly mixed with 10.16 g. 98% sulfuric acid in a container at ambient temperature and pressure. A mixture of isobutylene and PAU para-xylene (0.30% isobutylene and 99.70% PAU para-xylene product stream) was placed in a buret and added drop-wise to the xylenes/sulfuric acid mixture over a 45 minute period. A high speed magnetic stirrer was used to provide sufficient mixing. The hydrocarbon phase was sampled and analyzed by GC at the end of the reaction. It was found that the xylenes product contained 99.75% para-xylene, 0.16% meta-xylene, 0.06% ethylbenzene and 0.03% ortho-xylene. Thus, it is demonstrated that the process of this invention may be successfully performed using a homogeneous catalyst.

EXAMPLE 5

This Example demonstrates the use of a mordenite zeolite catalyst for purifying para-xylene. A mixture of 0.5% isobutylene and 99.5% PAU para-xylene product (99.70% para-xylene, 0.15% meta-xylene, 0.10% ethylbenzene, 0.05% ortho-xylene) was prepared. 3.02 Grams of the mixture was brought into contact with 1.09 g. of a mordenite extrudate obtained from UOP Inc. in a sealed bottle at ambient temperature and pressure for 2 hours. According to GC analysis, the xylenes product contained 99.76% para-xylene, 0.15% meta-xylene, 0.07% ethylbenzene, 0.03% ortho-xylene. It is thus demonstrated that another catalyst may be used in the process of this invention.

Many modifications may be made in the process of the present invention without departing from their spirit and scope, which are defined only in the appended claims. For example, one skilled in the art may find that a certain combination of alkylating agent and catalyst may give particularly advantageous results. Or one of ordinary skill in the art may determine that certain embodiments of the present inventive process if used in series may give a para-xylene product of extraordinary purity.

We claim:

1. A reactive purification process for producing at least 99.5 wt. % para-xylene from a mixture of isomers of xylene which contains more than about 90 wt. % para-xylene and which has been produced by a process exclusive of a selective alkylation process consisting essentially of the steps of:

(a) alkylating substantially all of the isomers of xylene other than para-xylene in the mixture of xylene isomers, wherein the mixture of xylene isomers contains between about 90 and 99.8 wt. % para-xylene, with an alkylating agent, while alkylating substantially none of the para-xylene; and (b) separating the para-xylene in at least 99.5 wt. % purity and at least greater than the concentration of para-xylene in the mixture of xylene isomers, from the alkylated xylene isomers to give the final product stream.

2. The process of claim 1 where in step (a) the alkylating is conducted in the presence of an acidic catalyst.

3. The process of claim 2 where the catalyst is a high surface area heterogeneous catalyst having at least 100 $m^2/g$.

4. The process of claim 2 where the catalyst is a homogeneous catalyst.

5. The process of claim 3 where in step (a) the alkylating is conducted in the presence of an acidic heterogeneous catalyst selected from the group consisting of proton-exchanged zeolites, bentonite clay, acid-treated clay, acidic alumina, proton-exchanged resins and mixtures thereof.

6. The process of claim 1 where in step (a) the alkylating is conducted at a temperature in the range of about 1 to about 300° C.

7. The process of claim 1 where in step (a) the alkylating agent contains at least one tertiary butyl moiety.

8. The process of claim 7 where the alkylating agent is selected from the group consisting of isobutylene, tertiary butyl chloride, tertiary butyl benzene, di-tertiary butyl hydroxyl toluene, isobutylene oligomers and mixtures thereof.

9. The purification process of claim 1 where the mixture of xylene isomers has between 95 and 99.9 wt. % para-xylene.

10. The purification process of claim 1 where the mixture of xylene isomers has between 98 and 99.9 wt. % para-xylene.

11. The purification process of claim 1 where alkylating step (a) and separating step (b) are each repeated in sequence at least once.

12. A reactive purification process for producing at least 99.5 wt. % para-xylene from a mixture of isomers of xylene which contains more than about 90 wt. % para-xylene and which has been produced by a process exclusive of a selective alkylation process consisting essentially of the steps of:

(a) alkylating substantially all of the isomers of xylene other than para-xylene in the mixture of xylene isomers, wherein the mixture of xylene isomers contains between about 90 and 99.8 wt. % para-xylene, with an alkylating agent having at least one tertiary butyl moiety in the presence of an acidic catalyst and with molecular contact between the catalyst and the xylene isomers, while alkylating substantially none of the para-xylene; and (b) separating the para-xylene in at least 99.5 wt. % purity and at least greater than the concentration of para-xylene in the mixture of xylene isomers, from the alkylated xylene isomers to give the final product stream.

13. The process of claim 12 where the catalyst is a high surface area heterogeneous catalyst having at least 100 m$^2$/g.

14. The process of claim 12 where the catalyst is a homogeneous catalyst.

15. The process of claim 12 where in step (a) the alkylating is conducted in the presence of an acidic heterogeneous catalyst selected from the group consisting of proton-exchanged zeolites, bentonite clay, acid-treated clay, acidic alumina, proton-exchanged resins and mixtures thereof.

16. The process of claim 12 where in step (a) the alkylating is conducted at a temperature in the range of about 1 to about 300° C.

17. The process of claim 12 where the alkylating agent is selected from the group consisting of isobutylene, tertiary butyl chloride, tertiary butyl benzene, di-tertiary butyl hydroxyl toluene, isobutylene oligomers and mixtures thereof.

18. The process of claim 12 where the alkylating agent is isobutylene and the catalyst is one which does not substantially dimerize the isobutylene.

19. The process of claim 12 in which the para-xylene produced at least 99.9 wt. % purity.

20. The process of claim 12 in which the alkylating is conducted from sub-atmospheric to about 1000 psig.

21. The process of claim 12 in which the alkylating is conducted at a liquid hourly space velocity (LHSV) between about 0.1 and about 100.

22. The purification process of claims 12 where the mixture of xylene isomers contains between about 90 and about 99.9 wt. % par-xylene.

23. The purification process of claim 12 where the mixture of xylene isomers has between 95 and 99.9 wt. % para-xylene.

24. The purification process of claim 12 where the mixture of xylene isomers has between 98 and 99.9 wt. % para-xylene.

25. The purification process of claim 12 where alkylating step (a) and separating step (b) are each repeated in sequence at least once.

26. A purification process for producing at least 99.5 wt. % para-xylene from a mixture of isomers of xylene having between 90 and 99.8 wt. % para-xylene and which has been produced by a process exclusive of a selective alkylation process consisting essentially of the steps of:

(a) alkylating substantially all of the isomers of xylene other than para-xylene in the mixture of xylene isomers, wherein the mixture of xylene isomers contains between about 90 and 99.8 wt. % para-xylene, with an alkylating agent having at least one tertiary butyl moiety at a temperature in the range of about 1 to about 300° C. in the presence of an acidic, heterogeneous catalyst with a high surface area of at least 200 m$^2$/g and with molecular contact between the catalyst and the xylene isomers, while alkylating substantially none of the para-xylene; and (b) separating the para-xylene in at least 99.5 wt. % purity and at least greater than the concentration of para-xylene in the mixture of xylene isomers, from the alkylated xylene isomers to give the final product stream.

27. The process of claim 26 where in step (a) the alkylating is conducted in the presence of an acidic heterogeneous catalyst selected from the group consisting of proton-exchanged zeolites, bentonite clay, acid-treated clay, acidic alumina, proton-exchanged resins and mixtures thereof.

28. The process of claim 26 where in step (a) the alkylating is conducted at a temperature in the range of about 1 to about 100° C.

29. The process of claim 27 where the alkylating agent is selected from the group consisting of isobutylene, tertiary butyl chloride, tertiary butyl benzene, di-tertiary butyl hydroxyl toluene, isobutylene oligomers and mixture thereof.

30. The process of claim 26 in which the para-xylene produced at least 99.9 wt. % purity.

31. The process of claim 26 in which the alkylating is conducted from sub-atmospheric to about 1000 psig.

32. The process of claim 26 in which the alkylating is conducted at a liquid hourly space velocity (LHSV) between about 0.1 and about 100.

33. The purification process of claim 26 where the mixture of xylene isomers has between 95 and 99.9 wt. % para-xylene.

34. The purification process of claim 26 where the mixture of xylene isomers has between 98 and 99.9 wt. % para-xylene.

35. The purification process of claim 26 where alkylating step (a) and separating step (b) are each repeated in sequence at least once.

* * * * *